United States Patent [19]
Woodruff et al.

[11] Patent Number: 5,792,796
[45] Date of Patent: Aug. 11, 1998

[54] METHODS FOR TREATING ANXIETY AND PANIC

[75] Inventors: Geoffrey Neil Woodruff, Dassels; Nicolas Steven Gee, Stansted; Lakhbir Singh, Haddenham; Jason Peter Brown, Stapleford, all of United Kingdom

[73] Assignee: Warner-Lambert Company, Morris Plains, N.J.

[21] Appl. No.: 445,398

[22] Filed: Jun. 6, 1995

Related U.S. Application Data

[63] Continuation-in-part of Ser. No. 281,285, Jul. 27, 1994, abandoned.

[51] Int. Cl.[6] ............... A61K 31/195; A61K 31/215
[52] U.S. Cl. ............... 514/561; 514/530; 514/529
[58] Field of Search ............... 514/561, 530, 514/529

[56] References Cited

U.S. PATENT DOCUMENTS

| | | |
|---|---|---|
| 4,024,175 | 5/1977 | Satzinger et al. |
| 4,087,544 | 5/1978 | Satzinger et al. |
| 5,084,479 | 1/1992 | Woodruff ............... 514/530 |
| 5,189,026 | 2/1993 | Costa et al. ............... 514/30 |

FOREIGN PATENT DOCUMENTS

| | | |
|---|---|---|
| 400665 | 12/1990 | European Pat. Off. |
| 92/22302 | 12/1992 | WIPO |
| 93/23383 | 11/1993 | WIPO |

OTHER PUBLICATIONS

D. Leiderman, et al., *Epilepsia*, 1993, 34:6, 45.
S.B. Ellis, et al., *Science*, 1988, 241:1661–4.
M. De Waard, et al., *J. of Biological Chem*, 1994, 269:9, 6716–6724.
K.S. DeJongh, et al., *J. of Biological Chem*, 1990, 265:25, 14738–14741.
P.-w Yuen, et al., *Bioorg & Med Chem Lett*, 1994, 4:6, 823–826.
H. Tokumaru, et al., *Eu J of Pharm–Molecular Pharm Section*, 1992, 227:363–370.
K.S. DeJongh, et al., *Proc Natl Acad Sci USA*, 1989, 86:8585–8589.
International Search Report for PCT/US95/08702, 1996.
Saletu, B., et al., *Intl J of Clinical Pharm, Therapy & Tox*, 1986, 24:7, 362–373.
Isom, L.L., et al., *Neuron*, 1994, 12:1183–1194.
Costall, B. et al., *Pharm. Biochem & Behav*, 1989, 32:777–785.
Costall, B. et al., *Br J Pharmacol*, 1989, 96:312P.
Field, M.J., et al., *Br. J Pharmacol*, 1991, 102:304P.
Goa, K.L., et al., *Drugs*, 1993, 46:3, 409–427.
Handley, S.L., et al., *Naunyn–Schmiedeberg's Arch Pharmacol*, 1984, 327:1–5.
Hill, D.R., et al., *Euro J of Pharm–Molecular Pharm Section*, 1993, 244:303–309.
Kilfoil, T., et al., *Neuropharmacology*, 1989, 28:9, 901–905.
Pellow, S., et al., *J. of Neuroscience Methods*, 1985, 14:149–167.
Singh, L., et al., *Proc Natl Acad Sci USA*, 1991, 88:1130–1133.
Suman–Chauhan, N., et al., *Euro J of Pharm–Molecular Pharm Section*, 1993, 244:293–301.
Andrews, J., et al., *Lancet*, 1990, 335:1114–1117.
Oommen, K., et al., *Neurology*, 1993, 43:2292–2298.

*Primary Examiner*—William R. A. Jarvis
*Attorney, Agent, or Firm*—Elizabeth M. Anderson

[57] ABSTRACT

The instant invention is novel uses of known cyclic amino acids. Such compounds as gabapentin are useful in the treatment of anxiety and in the treatment and/or prevention of panic attacks.

4 Claims, 4 Drawing Sheets

▨ UNPUNISHED  ▨ PUNISHED

METHODS FOR TREATING ANXIETY AND PANIC

CROSS-REFERENCE TO RELATED APPLICATION

This is a continuation-in-part of U.S. application Ser. No. 08/281,285 filed Jul. 27, 1994 now abandoned.

BACKGROUND OF THE INVENTION

The present invention relates to novel therapeutic uses of a known compound, gabapentin, its derivatives, and pharmaceutically acceptable salts. The present invention concerns a method for treating and/or preventing anxiety in a mammal in need of such treatment. It also concerns treating and/or preventing panic attacks in a mammal.

U.S. Pat. No. 5,084,479 concerns a method for treating neurodegenerative disorders.

Such neurodegenerative disorders are, for example, Alzheimer's disease, Huntingdon's disease, Parkinson's disease, and Amyotrophic Lateral Sclerosis. It also covers treating those neurodegenerative disorders termed acute brain injury. These include but are not limited to: stroke, head trauma, and asphyxia.

Stroke refers to a cerebral vascular disease or a cerebral vascular incident (CVA) and includes acute thromboembolic stroke. Stroke includes both focal and global ischemia. Also included are transient cerebral ischemic attacks and other cerebral vascular problems accompanied by cerebral ischemia. It is also useful in a patient undergoing specifically carotid endarterectomy or in general other cerebrovascular or vascular surgical procedures or diagnostic vascular procedures including cerebral angiography and the like.

Other incidents are spinal cord trauma or injury from general anoxia, hypoxia, hypoglycemia, hypotension as well as similar injuries seen during procedures from embole, hyperfusion, and hypoxia.

U.S. Pat. No. 4,024,175 and its divisional U.S. Pat. No. 4,087,544 cover the compounds of the instant invention, methods for preparing them, and several uses thereof. The uses disclosed are: protective effect against cramp induced by thiosemicarbazide; protective action against cardiazole cramp; the cerebral diseases epilepsy, faintness attacks, hypokinesia, and cranial traumas; and improvement in cerebral functions. The compounds are useful in geriatric patients. The patents are hereby incorporated by reference.

There is no disclosure in the above references to make obvious the present invention of novel uses of compounds of U.S. Pat. No. 4,024,175 to treat anxiety.

Gabapentin (Neurontin®) is a structural analogue of γ-aminobutyric acid (GABA), the major inhibitory neurotransmitter in mammalian brain. However, unlike GABA, it readily penetrates the blood-brain barrier and it does not interact with either $GABA_A$ or $GABA_B$ receptors (Bartoszyk D. G. and Reimann W. (1985), *Preclinical characterization of the anticonvulsant gabapentin*. In: 16th Epilepsy International Congress. Abstracts (Ciba-Geigy, Basel), Page 1). It has been shown to possess anticonvulsant activity in a wide range of animal seizure models. The spectrum of anticonvulsant activity for gabapentin predicted from these preclinical studies includes partial seizures and generalized tonic-clonic seizures. This has been confirmed in clinical studies (Goe K. L., Sorkin E. M. Gabapentin: A review of its pharmacological properties and clinical potential in epilepsy. *Drug Evaluation*, 46(3):409–427 (1993)). Patent Application WO 93/23383 covers gamma aminobutyric acid (GABA) and L-glutamic acid analogs for seizure treatment. It also discloses a treatment of depression, anxiety, and psychosis.

SUMMARY OF THE INVENTION

Gabapentin is currently under clinical use as an adjunctive treatment of partial seizures and partial seizures with secondary generalization in patients not satisfactorily controlled by or intolerant to conventional therapies. The mode of action of gabapentin was previously unknown but was thought to involve a novel, yet undefined, mechanism of antiepileptic action involving affinity for a previously unidentified binding site in the brain (Hill D. R., et al., Localization of [³H] gabapentin to a novel site in rat brain: autoradiographic studies. *Eur. J. Pharmacol.-Mol. Pharmacol. Sec.*, 244:303–309 (1993) and [³H] -Gabapentin binds to a novel site in rat cortical syneptic plasma membranes (Suman-Chaukan N., et al., *British Journal of Pharmacoloqy Proceedings Supplement*, 71P:Jul. 10–12, 1991)

We have now purified the gabapentin binding protein and determined the sequence of the first ten amino acid residues (EPFPSAVTIK). From this result we deduce that the gabapentin binding protein is an $\alpha_2\delta$ subunit of a brain calcium channel. Further compounds interacting with the $\alpha_2\delta$ subunit of the $Ca^{2+}$ channel will have anxiolytic, antipanic, and anticonvulsant activity. We have now discovered that gabapentin, isobutylGABA, and similar compounds bind to the [³H] gabapentin binding protein in rat, pig, and human brain.

In the present study we have examined gabapentin in four animal models.

The instant invention is a new use of the known compound gabapentin (Neurontin®); chemical name 1-(aminomethyl)cyclohexaneacetic acid. The compound is useful as an anxiolytic and as an agent in treating and/or preventing panic attacks.

DETAILED DESCRIPTION

Figure 1:
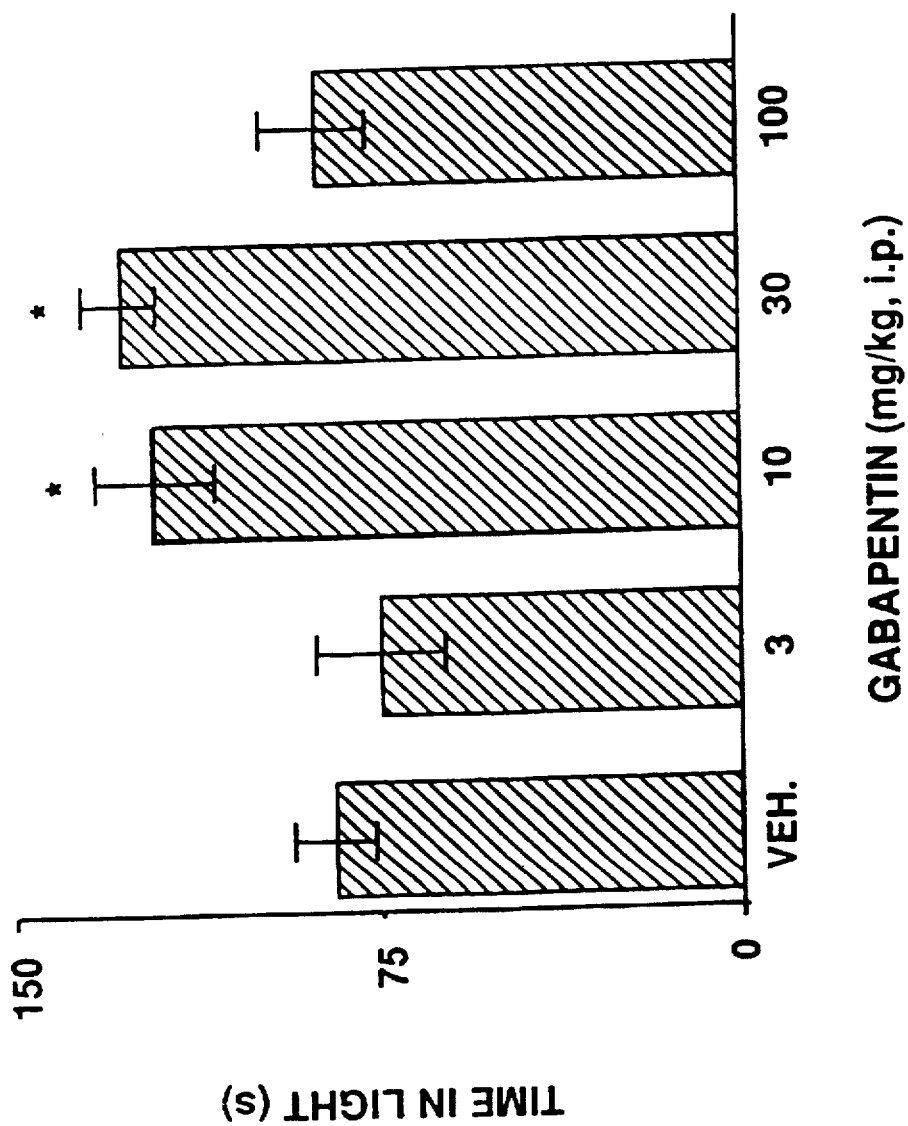
FIG. 1 shows the effect of gabapentin in the mouse light/dark box.

The present invention relates to novel methods of treating anxiolytic diseases or panic in a mammal in need of such treatment. The treatment comprises administering in unit dosage form a therapeutically effective amount of a compound of formula

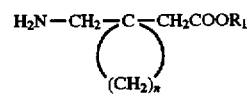

wherein $R_1$ is hydrogen or a lower alkyl and n is 4, 5, or 6 or a pharmaceutically acceptable salt thereof. The term lower alkyl includes straight or branched chain alkyl groups of up to 8 carbon atoms.

Preferred compounds of Formula I above include but are not limited to 1-aminomethyl-1-cyclohexane-acetic acid, ethyl 1-aminomethyl-1-cyclohexane-acetate, 1-aminomethyl-1-cycloheptane-acetic acid, 1-aminomethyl-1-cyclopentane-acetic acid, methyl 1-aminomethyl-1-cyclohexane-acetate, n-butyl 1-aminomethyl-1-cyclohexane-acetate, methyl 1-aminomethyl-1-cycloheptane-acetate, n-butyl 1-aminomethyl-1-cycloheptane-acetate, toluene sulfonate, 1-aminomethyl-1-cyclopentane-acetate, benzene-sulfonate, and n-butyl 1-aminomethyl-1-cyclopentane-acetate.

The most preferred compound is 1-aminomethyl-cyclohexane acetic acid (gabapentin).

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; isotonic saline; and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primary liquid composition. The most satisfactory compositions are those in which a much higher proportion of the active ingredient is present.

Routes of administration of the subject compound or its salts are oral or parenteral. For example, a useful intravenous dose is between 5 and 50 mg and a useful oral dosage is between 50 to 600 mg, preferably between 20 and 200 mg.

A unit dosage form of the instant invention may also comprise other compounds useful in the therapy of anxiety and diseases involving anxiety.

The advantages of using the compounds of Formula I, especially gabapentin, in the instant invention include the relatively nontoxic nature of the compound, the ease of preparation, the fact that the compound is well tolerated, and the ease of IV administration of the drug. Furthermore, the drug is not metabolized in the body.

The subjects used herein are mammals, including humans.

The usefulness of compounds of Formula I above and the salts thereof as agents for anxiety and for panic is demonstrated in standard pharmacological test procedures.

MATERIAL AND METHODS

Animals

Male Hooded Lister rats (200-250 g) were obtained from Interfauna (Huntingdon, UK) and male TO mice (20-25 g) were obtained from Bantin and Kingman (Hull, UK). Both rodent species were housed in groups of six. Ten Common Marmosets (Callithrix Jacchus) weighing between 280 and 360 g, bred at Manchester University Medical School (Manchester, UK) were housed in pairs. All animals were housed under a 12-hour light/dark cycle (lights on at 07.00 hour) and with food and water ad libitum.

Drug Administration

Drugs were administered either intraperitoneally (IP) or subcutaneously (SC) 40 minutes before the test in a volume of 1 mL/kg for rats and marmosets and 10 mL/kg for mice.

Mouse Light/Dark Box

The apparatus was an open-topped box, 45 cm long, 27 cm wide, and 27 cm high, divided into a small (2/5) and a large (3/5) area by a partition that extended 20 cm above the walls (Costall B., et al., Exploration of mice in a black and white box: validation as a model of anxiety. *Pharmacol. Biochem. Behav.*, 32:777-785 (1989)).

There was a 7.5×7.5 cm opening in the center of the partition at floor level. The small compartment was painted black and the large compartment white. The white compartment was illuminated by a 60-W tungsten bulb. The laboratory was illuminated by red light. Each mouse was tested by placing it in the center of the white area and allowing it to explore the novel environment for 5 minutes. The time spent in the illuminated side was measured (Kilfoil T., et al., Effects of anxiolytic and anxiogenic drugs on exploratory activity in a simple model of anxiety in mice. *Neuropharmacol.*, 28:901-905 (1989)).

Rat Elevated X-Maze

A standard elevated X-maze (Handley S. L., et al., Effects of alpha-adrenoceptor agonists and antagonists in a maze-exploration model of 'fear'-motivated behavior. *Naunyn-Schiedeberg's Arch. Pharmacol.*, 327:1-5 (1984)), was automated as previously described (Field, et al., Automation of the rat elevated X-maze test of anxiety. *Br. J. Pharmacol.*, 102(Suppl):304P (1991)). The animals were placed on the center of the X-maze facing one of the open arms. For determining anxiolytic effects the entries and time spent on the end half sections of the open arms was measured during the 5-minute test period (Costall, et al., Use of the elevated plus maze to assess anxiolytic potential in the rat. *Br. J. Pharmacol.*, 96(Suppl):312P (1989)).

Marmoset Human Threat Test

The total number of body postures exhibited by the animal towards the threat stimulus (a human standing approximately 0.5 m away from the marmoset cage and staring into the eyes of the marmoset) was recorded during the 2-minute test period. The body postures scored were slit stares, tail postures, scent marking of the cage/perches, piloerection, retreats, and arching of the back. Each animal was exposed to the threat stimulus twice on the test day before and after drug treatment. The difference between the two scores was analyzed using one-way analysis of variance followed by Dunnett's t-test. All drug treatments were carried out SC at least 2 hours after the first (control) threat. The pretreatment time for each compound was 40 minutes.

Rat Conflict Test

Rats were trained to press levers for food reward in operant chambers. The schedule consisted of alternations of four 4-minute unpunished periods on variable interval of 30 seconds signalled by chamber lights on and three 3-minute punished periods on fixed ratio 5 (by footshock concomitant to food delivery) signalled by chamber lights off. The degree of footshock was adjusted for each rat to obtain approximately 80% to 90% suppression of responding in comparison with unpunished responding. Rats received saline vehicle on training days.

RESULTS

The Mouse Light/Dark Box

The IP administration of gabapentin (3–100 mg/kg), 40 minutes before test, at doses of 10 and 30 mg/kg increased the time spent by mice in the illuminated side of the box, indicating an anxiolytic-like action (FIG. 1). However, the effect disappeared at the highest dose of 100 mg/kg gabapentin (FIG. 1).

The Rat Elevated X-Maze

Figure 2:
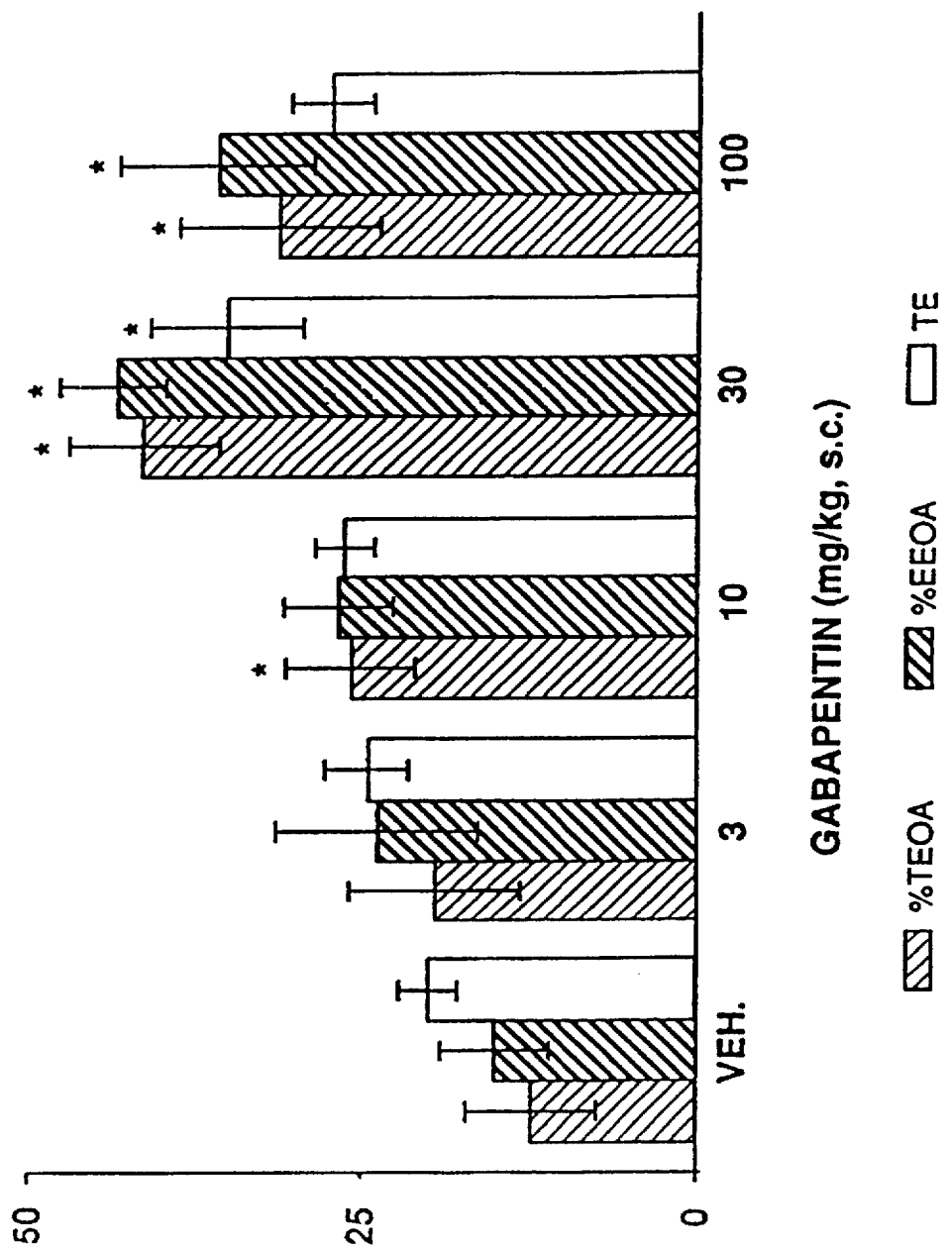
FIG. 2 shows the effect of gabapentin in the rat elevated X-maze.

The subcutaneous administration of gabapentin (3–100 mg/kg) increased the percent time spent (%TEOA) and percent entries (%EEOA) made onto the end half sections of the open arms (FIG. 2). These increases indicate an anxiolytic-like action. Furthermore, an increase in total entries was also observed at 30 mg/kg.

The Marmoset Human Threat Test

Figure 3:
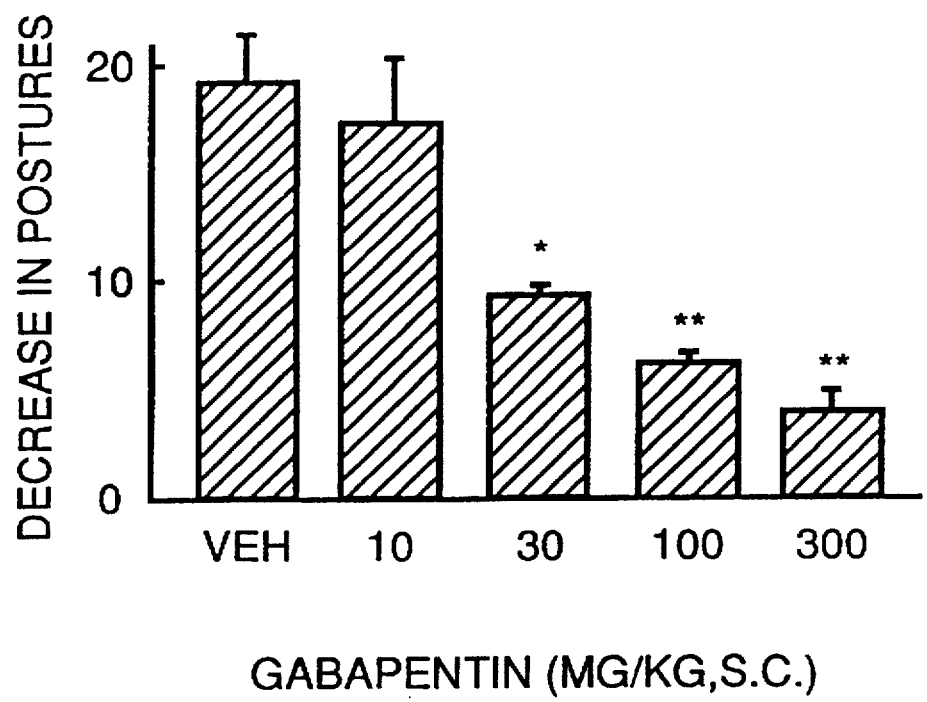
FIG. 3 shows the effect of gabapentin in the human marmoset threat test.

The subcutaneous administration of gabapentin (10–300 mg/kg) decreased the number of postures emitted by marmosets in response to a human threat (FIG. 3). This indicates an anxiolytic-like action. In this test, the activity of gabapentin was maintained over a wide dose range.

Rat Conflict Test

Figure 4A:
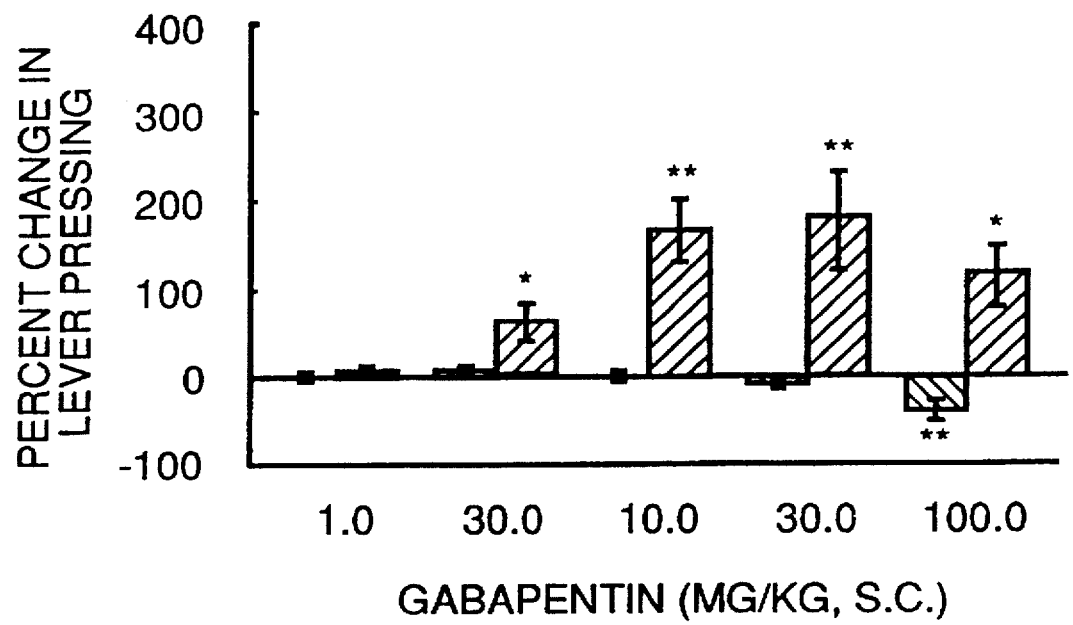
FIG. 4A and 4B show the effect of gabapentin and CDP in the rat conflict test.
Figure 4B:
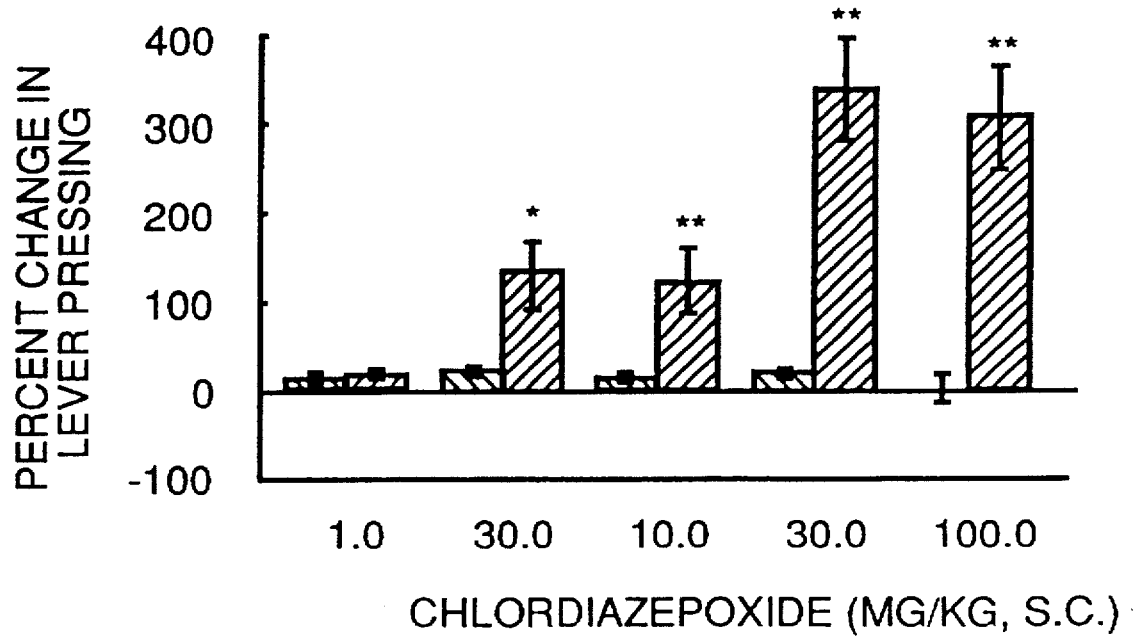

The administration of gabapentin 40 minutes before test dose-dependently (1–100 mg/kg) increased lever pressing in the punished period with a minimum effective dose of 3 mg/kg producing a 65% increase. A maximal effect (179% increase) was observed with 30 mg/kg. At the highest dose tested (100 mg/kg), a reduction in lever pressing (37.4%) was noted in the unpunished period, indicating sedation/ataxia, which may account for the apparent reduction in the effect observed in the punished phase. Similarly, chlordiazepoxide (1–100 mg/kg) dose-dependently increased lever pressing in the punished period with an MED of 3 mg/kg producing a 128.4% increase. A maximal effect (330.0% increase) was observed with 30 mg/kg. Unpunished responding was not reduced at any of the doses tested (FIGS. 4a and 4b).

Further, it has been shown that the effects of gabapentin, i.e., anticonvulsant and anxiolytic activity, can be reversed by D-serine. This reversal of the activity of D-serine showed these properties share a common mechanism of action. It does not involve a direct interaction between D-serine and gabapentin at the glycine/NMDA receptor complex as previous radioligand binding studies showed that gabapentin does not bind to the glycine/NMDA receptor (Suman-Chanhan, et al., *Eur. J. Pharmacol.-Mol. Pharmacol. Sec.*, 244:293–301 (1993).

BINDING OF GABAPENTIN TO THE $\alpha_2\delta$ SUBUNIT OF A CALCIUM CHANNEL.

Summary The partial N-terminal sequence of a pig brain [$^3$H] gabapentin binding protein has been determined. The sequence of the first ten residues, EPFPSAVTIK is identical to the N-terminal sequence of the mature $\alpha_2\delta$ subunit of the L-type $Ca^{2+}$ channel from rabbit skeletal muscle. The distribution of [$^3$H] gabapentin binding sites in rat tissues was broadly similar to that for dihydropyridine-sensitive $Ca^{2+}$ channels, as defined by [$^3$H] nitrendipine. The rank order of potency of ligands acting at the muscle [$^3$H] gabapentin binding site was consistent with that reported previously for CNS sites. [$^3$H] Gabapentin is the first pharmacological agent described that interacts with an $\alpha_2\delta$ subunit of a $Ca^{2+}$ channel. This suggests that modulation of voltage-dependent neuronal $Ca^{2+}$ channels is important to the antiepileptic action of gabapentin.

Materials

Pig brains were obtained from the local abattoir and transported to the laboratory on ice. Buffer components were obtained either from Sigma Chemical Company, Poole, Dorset, UK or from FSA Supplies, Loughborough, Leicestershire, UK. [$^3$H] Gabapentin (57.7 Ci/mmol) was custom synthesized by Amersham International, Amersham, Bucks, UK. Unlabeled gabapentin and the enantiomers of 3-isobutyl GABA were obtained from Warner-Lambert, Ann Arbor, Mich., USA. [$^3$H] Nitrendipine (75.3 Ci/mmol) was obtained from DuPont (UK) Ltd, Stevenage, Herts, UK.

Methods

Binding of [$^3$H] gabapentin to membranes was performed as described by Suman Chauhan, et al., *Eur. J. Pharmacol*, 244:293 (1993). [$^3$H] Nitrendipine binding was carried out at room temperature for 30 minutes in 50 mM Tris/150 mM NaCl/2.5 mM $CaCl_2$ and reactions were terminated by rapid filtration through GF/B filters. Nonspecific binding was defined as that obtained in the presence of 1 µM nifedipine. Preparation of $P_2$ membrane fractions and purification of the [$^3$H] gabapentin binding protein was as described by Gee, et al., 1994, (submitted) except that the active fractions from Sephacryl S400 were further fractionated on a $Cu^{2+}$-charged iminodiacetic acid-sepharose column. The final sample of purified protein (Approx. 5 µg) was electrophoresed in a 10% polyacrylamide gel and transferred to an immobilon P membrane. The blot was stained with Coomassie Blue and the 130 kDa band excised and sequenced on an Applied Biosystems 477A Sequencer.

Results

Protein sequencing. An N-terminal sequence determination was made on each of two different preparations of the purified pig [$^3$H] gabapentin binding protein. The sequence obtained for the first ten cycles was EPFPSAVTIK. A search of the GenBank database revealed 100% homology with the first ten residues of the mature $\alpha_2\delta$ subunit of the rabbit skeletal muscle L-type calcium channel (Ellis, et al., *Science* 241:1661 (1988)).

Distribution of [$^3$H] cabapentin binding sites in the rat. Radioligand binding assays using either [$^3$H] gabapentin or [$^3$H] nitrendipine were carried out using membranes prepared from a range of rat tissues. Relatively high levels of [$^3$H] gabapentin binding sites were observed in skeletal muscle. Moderately high levels were found in cerebral cortex and cerebellum, with lower levels in forebrain and heart. Trace amounts of [$^3$H] gabapentin binding sites were found in lung, spleen, liver, and kidney but pancreas and intestine were devoid of activity. The distribution of dihydropyridine-sensitive L-type $Ca^{2+}$ calcium channels, as defined by [$^3$H] nitrendipine, was broadly similar to that for [$^3$H] gabapentin, although detailed differences in the relative amounts of radioligand binding in certain tissues were observed.

The partial N-terminal sequencing data indicates that the [$^3$H] gabapentin binding protein from pig brain is an $\alpha_2\delta$ subunit of a voltage-dependent $Ca^{2+}$ channel.

DESCRIPTION OF THE DRAWINGS

FIG. 1. Effect of Gabapentin in the Mouse Light/Dark Box Gabapentin was administered IP 40 minutes before the test. The time spent in the light side of the light/dark box was measured. Results are shown as the mean (vertical bars represent ±SEM) of 10 animal per group.

*Significantly different from the vehicle (VEH) treated group, p <0.05 (ANOVA followed by Dunnett's t-test).

FIG. 2. Effect of Gabapentin in the Rat Elevated X-Maze Gabapentin was administered SC 40 minutes before test. The percent time spent (%TOEA) and percent entries made (%EEOA) on to the end half sections of the open arms, and the total number of entries (TE) were measured. Results are shown as the mean (vertical bars represent ±SEM) of 10 animals per group.

*Significantly different from vehicle-treated controls, p <0.05 (ANOVA followed by Dunnett's t-test).

FIG. 3. Effect of Gabapentin in the Marmoset Human Threat Test

Each animal was exposed to a 2-minute threat stimulus before and after dosing. Test compounds were administered SC 40 minutes before test. Results are shown as percent decrease in postures (vertical bars represent ±SEM) in 5 to 6 animals per group. *Significantly different from mean day controls, p <0.05 (ANOVA followed by Dunnett's t-test).

FIG. 4. Effect of Gabapentin and CDP in the Rat Conflict Test, and of Gabapentin in the Marmoset Human Threat Test Gabapentin or chlordiazepoxide (CDP) were administered 40 minutes before test. The results are expressed as mean percent increase or decrease of lever pressing (vertical bars represent ±SEM) of at least 5 animals per group on test day compared with mean performances obtained the 2 previous days following vehicle administration. Significantly different from previous control days

*p <0.05, **p <0.01 (paired Student t-test).

The results presented in the figures show that in addition to possessing anticonvulsant activity, gabapentin also shows potent anxiolytic-like action in animals. Thus, it showed good anxiolytic-like effects in the mouse light-dark box, the rat elevated X-maze, the rat conflict test, and the marmoset human threat test.

The dose range over which the anxiolytic-like effect of gabapentin was observed is similar to that producing anticonvulsant activity in animals. In the rat elevated X-maze and the marmoset human threat test, the magnitude of the effect was similar to that observed with benzodiazepine anxiolytics (Costall, et al., 1988; Singh, et al., 1991). The present data further shows that gabapentin produces a good anxiolytic-like effect in the rat conflict test. Most nonbenzodiazepine ligands that induce potent anxiolytic-like effects in the rat elevated X-maze and the marmoset human threat test show much weaker activity in shock-induced conflict tests. The ability of gabapentin to induce a good disinhibition of conflict behavior may represent an advantage over compounds such as buspirone and those currently undergoing clinical investigation for treatment of anxiety but are weakly active in this test (e.g., $CCK_B$ and $5-HT_3$ receptor antagonists; see Broekkamp, et al., 1989 for review; Singh, et al., 1991).

The results from the human threat test particularly suggest a role for gabapentin in the treatment of panic.

Examples of formulations of the subject compounds or salts thereof are illustrated by the following examples.

EXAMPLE 1

Injectables 1 mg to 100 mg/mL

Gabapentin

Water for Injection USP q.s.

The compound or a suitable salt thereof is dissolved in water and passed through a 0.2-micron filter. Aliquots of the filtered solution are added to ampoules or vials, sealed and sterilized.

EXAMPLE 2

Capsules 50 mg, 100 mg, 200 mg, 300 mg or 400 mg

Gabapentin, 250 g

Lactose USP, Anhydrous q.s. or 250 g

Sterotex Powder HM, 5 g

Combine the compound and the lactose in a tumble blend for 2 minutes, blend for 1 minute with the intensifier bar, and then tumble blend again for 1 minute. A portion of the blend is then mixed with the Sterotex powder, passed through a #30 screen and added back to the remainder of the blend. The mixed ingredients are then blended for 1 minute, blended with the intensifier bar for 30 seconds, and tumble blended for an additional minute. The appropriately sized capsules are filled with 141 mg, 352.5 mg, or 705 mg of the blend, respectively, for the 50 mg, 125 mg, and 250 mg containing capsules.

EXAMPLE 3

Tablets 5 mg, 100 mg, 200 mg, 300 mg, 400 mg, 500 mg or 600 mg

Gabapentin, 125 g

Corn Starch NF, 200 g

Cellulose, Microcrystalline, 46 g

Sterotex Powder HM, 4 g

Purified Water q.s. or 300 mL

Combine the corn starch, the cellulose, and the compound together in a planetary mixer and mix for 2 minutes. Add the water to this combination and mix for 1 minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for 5 minutes by drum rolling. Compressed tablets of 150 mg, 375 mg, and 750 mg, respectively, of the total mix are formed with appropriate sized punches the 50 mg, 125 mg, or 50 mg containing tablets.

We claim:

1. A method for treating anxiety which comprises administering a therapeutically effective amount of a compound of formula

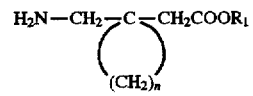

wherein $R_1$ is hydrogen or a lower alkyl and n is 4, 5, or 6 or a pharmaceutically acceptable salt thereof, in unit dosage form, to a mammal in need of said treatment.

2. A method of treating or preventing panic which comprises administering a therapeutically effective amount of a compound of formula

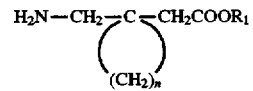

wherein $R_1$ is hydrogen or a lower alkyl and n is 4, 5, or 6 or a pharmaceutically acceptable salt thereof, in unit dosage form, to a mammal in need of said treatment or prevention.

3. A method according to claim 1 or claim 2 wherein the compound is gabapentin or a pharmaceutically acceptable salt thereof.

4. A method according to claim 1 or claim 2 wherein an individual dose is 5 mg to 50 mg parenterally or 50 to 600 mg enterally of the compound or a pharmaceutically acceptable salt thereof is administered.

* * * * *